United States Patent [19]

Winters et al.

[11] Patent Number: 5,338,770

[45] Date of Patent: * Aug. 16, 1994

[54] GAS PERMEABLE THROMBO-RESISTANT COATINGS AND METHODS OF MANUFACTURE

[75] Inventors: Suzanne Winters, Salt Lake City; Kenneth A. Solen, Orem; Clifton G. Sanders, Salt Lake City; JD Mortensen, Sandy; Gaylord Berry, Salt Lake City, all of Utah

[73] Assignee: Cardiopulmonics, Inc., Salt Lake City, Utah

[*] Notice: The portion of the term of this patent subsequent to Nov. 16, 2010 has been disclaimed.

[21] Appl. No.: 509,063

[22] Filed: Apr. 12, 1990

Related U.S. Application Data

[63] Continuation-in-part of Ser. No. 215,014, Jul. 5, 1988, Pat. No. 5,262,451, which is a continuation-in-part of Ser. No. 204,115, Jun. 8, 1988, Pat. No. 4,850,958.

[51] Int. Cl.$^5$ .................. A01N 1/00; A61M 25/00
[52] U.S. Cl. .................. 523/112; 530/812; 530/815; 530/816; 604/265; 604/266
[58] Field of Search ............ 523/112; 530/812, 815, 530/816; 604/265, 266; 204/192.36, 192.37

[56] References Cited

U.S. PATENT DOCUMENTS

| | | | |
|---|---|---|---|
| 3,453,194 | 7/1969 | Bennett et al. | 525/474 |
| 3,639,141 | 2/1972 | Dyck | 117/47 A |
| 3,826,678 | 7/1974 | Hoffman | 117/81 |

(List continued on next page.)

FOREIGN PATENT DOCUMENTS

| | | | |
|---|---|---|---|
| 0054919 | 6/1982 | European Pat. Off. | A61L 17/00 |
| 0152699 | 2/1984 | European Pat. Off. | A61L 33/00 |
| 0263184 | 3/1986 | European Pat. Off. | G01N 33/545 |
| 0335972 | 11/1986 | European Pat. Off. | A61L 33/00 |
| 0332261 | 3/1988 | European Pat. Off. | A61L 33/00 |
| 0351314 | 7/1988 | European Pat. Off. | A61L 33/00 |
| 0354061 | 8/1988 | European Pat. Off. | A61M 1/34 |
| 0357242 | 8/1988 | European Pat. Off. | A61L 33/00 |
| 0404683 | 6/1989 | European Pat. Off. | A61L 33/00 |
| 0423369A1 | 4/1990 | European Pat. Off. | A61M 1/18 |
| 54-135495 | 4/1978 | Japan | A61M 1/03 |
| WO88/02623 | 4/1988 | PCT Int'l Appl. | A61F 2/54 |
| WO90/01305 | 7/1989 | PCT Int'l Appl. | A61F 2/02 |
| WO91/12886 | 2/1990 | PCT Int'l Appl. | B01D 15/08 |
| WO91/16932 | 4/1990 | PCT Int'l Appl. | A61L 33/00 |
| 1391028 | 6/1972 | United Kingdom | C07G 7/00 |
| 2167665A | 12/1984 | United Kingdom | A61F 2/00 |
| 2001663 | 1/1991 | United Kingdom | C08G 69/48 |

*Primary Examiner*—Peter Szekely
*Attorney, Agent, or Firm*—Workman Nydegger Jensen

[57] ABSTRACT

The present invention is directed to thrombo-resistant coatings for use with gas permeable biomedical devices and implants. The coatings include a siloxane surface onto which a plurality of amine functional groups have been bonded. Covalently bonded to the amine functional groups are a plurality of poly(ethylene oxide) chains, such that a single poly(ethylene oxide) chain is bonded to a single amine functional group. A quantity of at least one bioactive molecule designed to counteract a specific blood-material incompatibility reaction is covalently bonded to the poly(ethylene oxide) chains, such that a single bioactive molecule is coupled to a single polyethylene oxide chain.

The methods of manufacturing the present invention include preparing a material having a siloxane surface onto which a plurality of amine functional groups have been bonded. This is preferably achieved by plasma etching with ammonia gas. The amine-containing siloxane surface is reacted with poly(ethylene oxide) chains terminated with functional groups capable of reacting with the amine groups on the siloxane surface. The material is then reacted with a solution of at least one bioactive molecule which counteracts a blood-material incompatibility reaction, such that a single bioactive molecule is coupled to a single poly(ethylene oxide) chain. The resulting siloxane surface is capable of resisting blood-material incompatibility reactions while maintaining high gas permeability.

33 Claims, No Drawings

U.S. PATENT DOCUMENTS

| | | | |
|---|---|---|---|
| 3,846,353 | 11/1974 | Grotta | 260/9 |
| 3,940,506 | 2/1976 | Heinecke | 427/38 |
| 3,969,240 | 7/1976 | Kolobow et al. | 210/22 |
| 3,992,495 | 11/1976 | Sano et al. | 264/22 |
| 4,093,515 | 6/1978 | Kolobow et al. | 195/1.8 |
| 4,170,559 | 10/1979 | Kroplinski et al. | 210/321 |
| 4,210,529 | 7/1980 | Petersen | 210/22 |
| 4,214,020 | 7/1980 | Ward et al. | 427/296 |
| 4,243,776 | 1/1981 | Marconi et al. | 525/420 |
| 4,483,901 | 11/1984 | Okita et al. | 428/315.5 |
| 4,521,564 | 6/1985 | Solomon et al. | 525/54.1 |
| 4,600,652 | 7/1986 | Solomon et al. | 428/423.3 |
| 4,613,517 | 9/1986 | Williams et al. | 427/2 |
| 4,613,665 | 9/1986 | Larm | 536/20 |
| 4,622,206 | 11/1986 | Torgeson | 422/48 |
| 4,666,668 | 5/1987 | Lidorenko et al. | 422/48 |
| 4,673,584 | 6/1987 | Nygren et al. | 427/2 |
| 4,770,852 | 9/1988 | Takahara et al. | 422/48 |
| 4,781,889 | 11/1988 | Fukasawa et al. | 422/48 |
| 4,806,595 | 2/1989 | Noishiki et al. | 525/54.2 |
| 4,810,784 | 3/1989 | Larm | 536/20 |
| 4,822,741 | 4/1989 | Banes | 435/300 |
| 4,828,561 | 5/1989 | Woodroof | 623/8 |
| 4,844,986 | 7/1989 | Karakelle et al. | 428/447 |
| 4,846,844 | 7/1989 | De Leon et al. | 623/66 |
| 4,861,830 | 8/1989 | Ward, Jr. | 525/92 |
| 4,872,867 | 10/1989 | Joh | 604/269 |
| 4,879,135 | 11/1989 | Greco et al. | 427/2 |
| 4,919,659 | 4/1990 | Horbett et al. | 623/1 |
| 5,004,461 | 4/1991 | Wilson | 604/265 |
| 5,013,717 | 5/1991 | Solomon et al. | 514/56 |
| 5,019,393 | 5/1991 | Ito et al. | 424/423 |
| 5,026,607 | 6/1991 | Kiezulas | 428/423.7 |
| 5,043,278 | 8/1991 | Nagaoka et al. | 530/812 |
| 5,053,048 | 10/1991 | Pinchuk | 623/1 |
| 5,053,453 | 10/1991 | Ku | 525/54.1 |
| 5,061,738 | 10/1991 | Solomon et al. | 523/100 |

GAS PERMEABLE THROMBO-RESISTANT COATINGS AND METHODS OF MANUFACTURE

The Related Applications

This application is a continuation-in-part of copending application Ser. No. 07/215,014, filed Jul. 5, 1988, now U.S. Pat. No. 5,262,451, which is a continuation-in-part of application Ser. No. 07/204,115, filed Jun. 8, 1988, now U.S. Pat. No. 4,850,958. Each of these patents is incorporated herein by specific reference.

BACKGROUND

1. The Field of the Invention

The invention relates to thrombo-resistant compositions for coating gas permeable polymers and to the methods of manufacturing such coatings so that the resulting product remains gas permeable and thrombo-resistant. More particularly, the present invention immobilizes at least one bioactive molecule, such as heparin, to a gas permeable siloxane surface in order to combat at least one blood-material incompatibility reaction.

2. The Prior Art

Over the years, a large number of medical devices have been developed which contact blood. The degree of blood contact varies with the device and its use in the body. For instance, catheters may briefly contact the blood, while implants, such as heart valves and vascular grafts, may contact blood for a number of years. Regardless of the device, blood contact with foreign materials initiates the process of thrombosis, which may be followed by formation of thromboemboli.

Adsorption of proteins is one of the first events to occur when blood contacts a foreign surface. The compositions and conformation of adsorbed proteins influence subsequent cellular responses such as platelet adhesion, aggregation, secretion, complement activation, and ultimately, the formation of cross-linked fibrin and thrombus. Thrombus formation is an obvious and potentially debilitating response to foreign material in contact with blood.

The initial protein layer at the blood-material interface is subject to denaturation, replacement, and further reaction with blood components. During this phase of protein adsorption, adsorbed fibrinogen is converted to fibrin. Fibrin formation is accompanied by the adherence of platelets and possibly leucocytes. The platelets become activated and release the contents of their granules. This activates other platelets, thereby resulting in platelet aggregation.

A thrombus eventually forms from entrapment of erythrocytes (red blood cells) and other blood constituents in the growing fibrin network. Thrombus growth can eventually lead to partial or even total blockage of the vascular channel and/or interference with the function of the device unless the thrombus is sheared off or otherwise released from the foreign surface as an embolus. Unfortunately, such emboli can be as dangerous as blockage of the vascular channel since emboli can travel through the bloodstream, lodge in vital organs, and cause infraction of tissues. Infarction of the heart, lungs, or brain, for example, can be fatal. Therefore, the degree to which the foreign material inhibits thrombus formation, embolization, and protein denaturation is a determinant of its usefulness as a biomaterial.

In the past, the thrombogenicity of biomedical implants has been treated by the administration of systemic anticoagulants such as heparin and warfarin. However, long-term anticoagulation therapy is not advisable due to the risk of hazardous side effects. Moreover, overdose of anticoagulants may cause lethal side reactions, such as visceral or cerebral bleeding. For these reasons, there have been extensive efforts to develop materials which can be used in biomedical devices or implants which can contact blood with minimal or no systemic anticoagulation therapy being necessary to avoid thrombus formation.

Many studies have attempted to produce a nonthrombogenic blood-contacting surface through immobilization of biologically active molecules onto the surface. Such bioactive molecules counteract various blood-material incompatibility reactions.

Surface modification of polymeric materials offers the advantage of optimizing the chemical nature of the blood/polymer interface while allowing a choice of the substrate to be based upon the necessary mechanical properties of the blood-contacting device.

The methods used to immobilize bioactive molecules onto blood-contacting surfaces fall into four general groups: physical adsorption, physical entrapment, electrostatic attraction, and covalent binding.

Surfaces incorporating bioactive molecules by physical adsorption or entrapment beneath the blood-contacting surface exhibit a significant degree of thrombo-resistance. However, depletion of the bioactive molecules into the blood environment causes the surface to rapidly lose its thrombo-resistant character. Entrained molecules diffuse to the surface which, along with physically adsorbed bioactives, are then "leached" from the surface into the blood plasma by mechanical and chemical mechanisms.

Similarly, electrostatically or ionically bound molecules are subject to partitioning and ion exchange between the blood-contacting surface and the electrolyte-rich plasma resulting in depletion. Covalently bound bioactive molecules resist depletion sufficiently to offer a potentially "long term" thrombo-resistant effect.

Numerous studies of covalent attachment of different biomolecules are available. These studies generally involve the covalent attachment of a single bioactive molecule, usually heparin, designed to counteract one aspect of the blood-material incompatibility reactions. Most studies have focused on covalently binding heparin to a blood-contacting surface. Heparin is the most effective anticoagulant in clinical use today. It is a highly sulfonated mucopolysaccharide containing a number of charged functional groups. Heparin enhances the inactivation of thrombin by antithrombin III, thereby inhibiting the conversion of fibrinogen to fibrin.

Most prior attempts to covalently bind heparin to a blood-contacting surface have severely decreased the activity of heparin. For example, heparin coupled to a blood-contacting surface through one of its carboxyl groups may lose up to 90% of its activity. Other systems, claiming covalent attachment of heparin, are actually heparin covalently bound to a coupling molecule which is subsequently ionically bound to the substrate.

Additional problems are encountered when the blood-contacting surface must also be gas permeable. Siloxane polymers are of particular interest in blood gas exchange devices because siloxane polymers not only possess certain inherent thrombo-resistant properties, but siloxane polymers also are gas permeable. However, siloxane polymers are relatively inert and pose a significant obstacle in modifying the surface in order to become more thrombo-resistant.

From the foregoing, it will be appreciated that what is needed in the art are thrombo-resistant compositions and methods which do not inhibit the gas permeability of the blood-contacting surface. Especially needed are methods for conferring thrombo-resistance to siloxane polymers.

It would be another important advancement in the art to provide gas permeable thrombo-resistant compositions and methods in which a bioactive molecule, such as heparin, is covalently bound to the gas permeable blood-contacting surface, thereby eliminating elution of the bioactive molecule into the blood plasma.

It would be a further advancement in the art to provide gas permeable thrombo-resistant compositions and methods in which the bioactive molecules retain their activity after immobilization on the gas permeable blood-contacting surface.

Such gas permeable thrombo-resistant compositions and methods are disclosed and claimed herein.

BRIEF SUMMARY AND OBJECTS OF THE INVENTION

The present invention is directed to gas permeable thrombo-resistant coatings for use with gas permeable biomedical devices and implants. A quantity of at least one bioactive molecule selected to counteract a specific blood-material incompatibility reaction is preferably immobilized onto the gas permeable polymeric surface of the device which contacts the blood.

Siloxane is the presently preferred substrate surface (that is, to which bioactive molecules are bonded), because the substrate itself is initially relatively thrombo-resistant. Moreover, siloxane is gas permeable, thereby enabling the coatings of the present invention to be used in a variety of gas permeable applications.

In order to overcome the inertness of the siloxane surface, functional groups, preferably amine groups, are introduced onto the siloxane surface. Amine functionalities are preferably introduced onto the siloxane surface by plasma etching with ammonia gas. It is also possible to introduce amine functionalities onto the siloxane surface by addition of ammonia gas during plasma polymerization of a siloxane monomer.

In one currently preferred embodiment of the present invention, the amine functional groups on the siloxane surface are reacted with an aqueous solution of poly(ethylene oxide) bis(glycidyl ether). Other poly(ethylene oxide) (hereinafter referred to as "PEO") derivatives which may be successfully used within the scope of the present invention are aqueous solutions of poly(ethylene oxide) bis(2-amino-1,4-benzoquinone). After such reaction occurs, the siloxane surface contains PEO chains coupled to the amine groups. The PEO spacer chains are presently preferred because the PEO tends to minimize protein adsorption.

The unbound terminal end groups on the PEO chains readily react with the amine groups found in many bioactive molecules. The desired bioactive molecule is covalently bonded to one end of the PEO chains in a reaction similar to the reaction which covalently bonds the other end of the PEO chain to the gas permeable siloxane surface.

Since the desired bioactive molecule is spaced away from the siloxane surface at one end of a long PEO chain, the bioactive molecule possesses an activity approaching the activity of the bioactive molecule in solution. Because of this mobility of the bioactive molecule near the blood-contacting surface of the polymer, the effectiveness of the bioactive molecule is substantially greater than the same bioactive molecule bound directly to the blood-contacting surface. At the same time, the serious risks associated with systemic anticoagulation therapy are avoided.

Typical bioactive molecules which may be immobilized on a gas permeable siloxane surface within the scope of the present invention include: heparin, ticlopidine, iloprost, prostaglandin $E_1$ ($PGE_1$), streptokinase, urokinase, and plasmin.

Heparin inhibits the blood incompatibility reaction resulting in clotting and thromboemboli formation by interacting with antithrombin III and thrombin to inhibit the conversion of fibrinogen to fibrin.

Ticlopidine, prostaglandin $E_1$, and synthetic prostaglandin analogues, such as iloprost, inhibit the activation of platelets either by minimizing aggregation or inhibiting activation and the release of the intracellular platelet activators. Each drug has a slightly different mode of action. Urokinase, streptokinase, and plasmin are serine proteases which lyse formed protein deposits and networks, which while not inhibiting thrombus formation, breakdown any formed fibrin.

The present invention is unique because it enables a gas permeable siloxane surface to be coated with one or more bioactive molecules covalently bound thereto.

It is, therefore, an object of the present invention to provide gas permeable thrombo-resistant compositions and methods of manufacture which counteract specific blood material incompatibility reactions.

Another important object of the present invention is to provide thrombo-resistant compositions for a blood-contacting siloxane surface which do not inhibit the gas permeability of the surface.

An additional important object of the present invention is to provide gas permeable thrombo-resistant compositions and methods in which bioactive molecules are covalently bound to the blood-contacting surface, thereby eliminating elution of the bioactive molecules into the blood plasma.

Still another object of the present invention is to provide gas permeable thrombo-resistant compositions and methods in which the bioactive molecules retain their activity after immobilization onto the blood-contacting surface.

These and other objects and features of the present invention will become more fully apparent from the following description and appended claims, or may be learned by the practive of the invention.

DETAILED DESCRIPTION OF THE PREFERRED EMBODIMENTS

The present invention provides a thrombo-resistant coating for use with a gas permeable blood-contacting surface of a medical device or implant. While it will immediately be appreciated that the present invention is applicable to a wide variety of other medical devices and implants, the coatings of the present invention are particularly suited for use with blood gas exchange devices. In any blood gas exchange device it is critical to both minimize thrombus and emboli formation, while at the same time preserving the gas exchange capabilities of the device.

Accordingly, for purposes of illustration, the coatings of the present invention are discussed with respect to one such blood gas exchange device (as described in the above-identified U.S. Pat. No. 4,850,958 entitled "Apparatus and Method for In Vivo Extrapulmonary Blood Gas Exchange"); however, it is not intended that the invention is to be construed as limited for use on only such a device.

A. Bioactive Molecules

To minimize the thrombo-resistant properties of any blood-contacting surface within the scope of the present invention, a quantity of at least one bioactive molecule which counteracts a specific blood-material incompatibility reaction is immobilized or linked to the blood-contacting surface.

The bioactive molecule is selected to inhibit blood material incompatibility reactions such as: coagulation and thrombus formation; platelet destruction, injury, entrapment, aggregation, and activation; complement activation; lysis of fibrin; and protein adsorption. Table I provides a summary of the various bioactive molecules which may be used within the scope of the present invention to combat blood-material incompatibility reactions.

TABLE I

| BLOOD INCOMPATIBILITY REACTION | BIOACTIVE SUBSTANCE | TYPE OF BIOACTIVITY |
| --- | --- | --- |
| Extrinsic coagulation pathway activation | Heparin | Interruption of the conversion of fibrinogen to fibrin |
| Platelet destruction and injury, adhesion, and aggregation | Prostaglandin $E_1$ and synthetic prostaglandin analogues | Inhibits platelet shape change, platelet factor release, secretion and aggregation |
|  | Ticlopidine | Protects platelets and inhibits platelet aggregation |
| Fibrin Formation | Plasmin | Lyses fibrin |
|  | Urokinase Streptokinase | Converts plasminogen to plasmin, general proteolytic enzyme. |
|  | TPA | Activates plasminogen |
| Complement activation | FUT-175 | Inhibits $Cl_r$, $Cl_s$, thrombin, and kallikrein |

Any of the various bioactive molecules immobilized onto the surface gives the blood-contacting surface a thrombo-resistant coating. The term "thrombo-resistant" is generally used herein to generically represent the action of inhibiting any of the blood incompatibility reactions discussed above. Thus, despite substantial surface contact with blood, thrombus formation on the surface of the medical device or implant (e.g., a blood gas exchange device) is inhibited or counteracted according to the compositions and methods within the scope of the present invention.

It will be appreciated that Table I lists only a few of the bioactive substances which inhibit the identified blood-material incompatibility reactions and that other bioactive substances may be used in accordance with the present invention to make a surface thrombo-resistant. As is discussed hereinafter, another important feature of the bioactive molecules used in the present invention is the availability of a primary amine (or other suitable functional groups) to react with the unbound functional end group on a molecule attached to the substrate surface.

B. Blood Gas Exchange Device

The blood gas exchange devices to which the present invention is particularly applicable include both sheet membrane and tubular membrane oxygenators. Numerous oxygenators of these types are well known in the prior art.

For purposes of illustration, one blood gas exchange device to which the present invention is applicable includes a dual lumen tube containing two coaxial lumens. The outer lumen opens into an airtight proximal chamber to which the proximal ends of a plurality of elongated gas permeable tubes are attached. The inner lumen extends past the outer lumen and passes among the gas permeable tubes. Both the inner lumen and the distal ends of gas permeable tubes open into an airtight distal chamber.

The device is inserted into the patient's venae cavae through an incision made in either the common femoral vein or the internal jugular vein. The gas permeable tubes are crimped in order to maintain the tubes in a spaced relation one from another so that the blood may flow freely between and around the tubes, thereby enhancing the blood surface contact with the gas permeable tubes.

One of either the inner or outer lumens is connected to a source of oxygen-rich gas. The other lumen is connected to an exhaust tube or other means for allowing the gas to flow out of the device. The oxygen-rich gas flows through the gas permeable tubes. As venous blood flows around the gas permeable tubes, oxygen passes from the tubes into the blood, thereby causing blood oxygenation, and carbon dioxide passes from the blood into the tubes and out of the body.

One of the primary goals of a blood gas exchange device (whether or not it has the specific configuration discussed above) is to maximize the gas transfer surface area in contact with the blood. Unfortunately, as the surface area of a foreign device in contact with blood increases, the risk of triggering a host of blood-material incompatibility reactions also increases.

Traditionally, as mentioned above, when a large quantity of blood contacts a foreign surface, systematic anticoagulants or thrombolytic agents are administered. Extreme care must be taken when administering any anticoagulants or thrombolytic agents to avoid the potential risk of serious hemorrhage both internally and externally. Thus, it is important that the blood-contacting surface of a blood gas exchange device is both gas permeable and thrombo-resistant. For these reasons, when the present invention is used with a blood gas exchange device, the blood-contacting surface is preferably constructed of a thin siloxane polymer.

C. Obtaining a Gas Permeable Siloxane Surface

In the blood-gas exchange device of the present invention, microporous hollow fibers coated with a plasma-polymerized siloxane are used as the substrate. The term "plasma" refers to a thermodynamically non-equilibrium state. The energized electrons in the field can interact with the organic monomer or gases which produce mainly free radicals and ions. Any object in the field is subject to a negative charge of its surface. Ions and free radicals will impact the object's surface and under certain conditions a "plasma" thin film will form on the surface.

Two opposing processes occur simultaneously during plasma discharge. In general, it can be said that the generation of free radicals in the vapor phase lead to the formation of thin films. However, at high power of field strength, ions are generally responsible for ablation or "etching" of the surface. Generally at very low gas or monomer flow rates there is little polymer deposition and the deposition rate decreases with increasing discharge power. At higher flow rates, the deposition increases (linearly), but reaches a maximum with increasing discharge power and then ablation becomes more predominant.

The amount and relative position of polymer deposition is influenced by at least three geometric factors: (1) location of the electrode and distribution of charge; (2) monomer flow; and (3) substrate position within the reactor relative to the glow region. In the case of hollow fibers which are pulled continuously through the plasma chamber, the influence of the substrate position is averaged over the length of the fibers. This is the currently preferred polymer deposition arrangement.

The population of energetic species that contribute to the direct formation of plasma polymer is not directly or uniquely related to the power input into the system. The intensity of a non-polymer forming plasma (i.e., plasma etching) is dependent on the combined factors of pressure and discharge power as well as on other factors of the discharge system such as distance between electrodes, surface area of electrodes, and total volume of the reactor.

Various parameters have been used to describe the energy input of plasma polymerization such as current density, current and voltage, or wattage. These parameters may have varying degrees of applicability to an inductively or capacitively coupled Radio Frequency ("RF") discharge system. However, such parameters are insufficient to describe the change in total volume of plasma and the plasma polymerization that takes place in the volume, although certain correlations can be found between the deposition rates and these parameters, but only for a given set of experimental conditions.

An important feature of the present invention, particularly for use with a blood oxygenator, is the creation of a smooth, continuous (pin-hole free) thin coating (less than 1 micron thick) over the pores of the hollow fiber. The thickness of this coating can be determined gravimetrically, and the continuity of the coating can be determined by the permeability. These factors, along with the chemical composition (i.e., carbon, silicone, oxygen, nitrogen percentages, determined by ESCA) are some of the values which change as plasma parameters are modified.

The chemical composition of the plasma coating affects the gas permeability. For example, as the cross-link density increases, the permeability decreases. Factors which affect the cross-link density include: pressure, power, flow rate, and position within the reactor. Gas permeability is also influenced by the plasma deposition thickness and the completeness of coverage of the pores.

The pressure, temperature, gas flow rates, exposure time, power, and other parameters in a plasma process are highly interdependent and highly dependent upon the size and geometry of the plasma chamber. The power per unit area is an important parameter in pre-producing controlling the chemical structure of the resulting polymer. However, since plasma polymerization and etching procedures and techniques are well known, a detailed discussion of each of the process parameters is not provided herein.

Plasma may be generated by a number of methods including combustion, flames, electric discharge, controlled nuclear reactions and shocks. The most obvious and commonly used is the electric discharge. Radio frequency ("RF") or microwave discharge are mainly used for polymerization reactions. for the commercial RF generators, the frequency is dictated by the Federal Communications Commission and is set at 13.56 MHz.

One currently preferred plasma machine used for the deposition of the siloxane membrane consists of a central bell jar with four peripheral vacuum chambers attached via glow zone pyrex tubing approximately 24 inches long. The RF discharge is coupled capacitively through two pair of copper electrodes on each arm. Therefore, each arm has two (2) glow zones.

The microporous hollow fiber substrate is pulled through from feed spools in the peripheral chambers through a system of pulleys such that the fiber passes through the glow tubes more than once is taken up on spools in the central bell jar. The vacuum, RF power, monomer flow rate, and fiber speed are all computer controlled.

The currently preferred operating parameters are to expose the polypropylene microporous hollow fiber to a siloxane monomer having a mass flow rate of about 12 $\mu$moles/second/arm at an absolute pressure of about 65 mtorr. The fiber is pulled through each arm at a speed of about 3.2 cm/sec. A radio frequency of 13.56 MHz at about 17 watts/arm is applied to the fiber.

The above conditions produce a cross-linked siloxane membrane on the polypropylene microporous hollow fiber on the order of about 0.5 to about 1.0 microns in thickness. When 1,3-divinyltetramethyl disiloxane is the siloxane monomer, the membrane has been found to have an oxygen permeability ranging from about $0.37 \times 10^{-4}$ cm$^3$/sec.cm$^2$.cm Hg to about $3.4 \times 10^{-4}$ cm$^3$/sec.cm$^2$.cm Hg and a carbon dioxide permeability ranging from $0.8 \times 10^{-4}$ cm$^3$/sec.cm$^2$.cm Hg to about $5.0 \times 10^{-4}$ cm$^3$/sec.cm$^2$.cm Hg. The permselectivity (ratio of permeabilities) of the membrane is in the range from about 2.5 to about 4.0.

When tetramethyl disiloxane is the siloxane monomer, the membrane has been found to have an oxygen permeability ranging from about $0.9 \times 10^{-4}$ cm$^3$/sec.cm$^2$.cm Hg to about $1.9 \times 10^{-4}$ cm$^3$/sec.cm$^2$.cm Hg and a carbon dioxide permeability ranging from about $3.5 \times 10^{-4}$ cm$^3$/sec.cm$^2$.cm Hg to about $5.2 \times 10^{-4}$ cm$^3$/sec.cm$^2$.cm Hg.

It will be appreciated that there are other methods for producing suitable siloxane coated hollow fibers. Nevertheless, the foregoing discussion is included to provide one skilled in the art with an understanding of one preferred method of producing suitable siloxane coated hollow fibers and typical parameters of such fibers.

D. Linking the Bioactive Molecules onto the Blood Contacting Surface

For purposes of illustration, reference will be made to "linking" or "immobilizing" bioactive molecules on the blood-contacting substrate surface of a blood gas exchange device. It will be readily appreciated that the principles and teachings of the present invention are generally applicable to most other medical devices and implants which contact blood and have a problem with thrombus and emboli formation.

Moreover, it will be appreciated that the term "immobilized" is being used in the sense that the bioactive molecules are covalently linked or "tethered" to a specific portion of the polymer substrate vis-a-vis free floating in the blood. Therefore, even though the bioactive molecules may not be directly attached to the blood-contacting surface (as discussed in greater detail below), the bioactive molecules are closely associated to the surface through a linkage such that the blood components contact the bioactive molecules as they come proximate to the blood-contacting surface.

Most of the bioactive molecules described above are capable of being immobilized to the blood-contacting surface of the blood gas exchange device through PEO coupling molecules. PEO is the preferred coupling molecule, because PEO itself functions to minimize protein adsorption. This property of PEO is believed to be due in part to PEO's unique hydrophobic and hydrophilic characteristics.

Because the blood-contacting surface of the blood-gas exchange device is preferably constructed of siloxane, the inherent inertness of the siloxane polymer minimizes thrombus formation. However, this same inherent inertness of the siloxane significantly complicates the method of immobilizing the bioactive molecules to the surface.

To overcome the inertness of the siloxane, functional groups are introduced on the siloxane surface. These functional groups provide distinct and predictable sites for reaction with PEO. The PEO chains are then coupled to the blood-contacting surface through the functional groups. In the currently preferred embodiment of the present invention, amine groups are introduced onto the siloxane surface.

1. Introduction of Amine Groups by Plasma Etching

One proposed method for introducing amine groups on the siloxane surface within the scope of the present invention involves plasma etching with ammonia gas. In the blood-gas exchange device of the present invention, microporous hollow fibers coated with a plasma-polymerized siloxane, described above, are used as the substrate. These fibers are subjected to additional plasma exposure in the presence of ammonia gas.

One plasma chamber used for plasma etching within the scope of the present invention has a volume of about 20,000 cm$^3$ and capacitively coupled plate-type electrodes. The siloxane plasma-coated fibers, having a surface area of about 2,100 cm$^2$, are exposed to ammonia having a flow rate in the range of from about 100 micromoles per second to about 300 micromoles per second, at an absolute pressure in the range from about 100 millitorr to about 200 mtorr. The exposure time ranges from about thirty (30) seconds to about fifteen minutes. The currently preferred exposure time is in the range from about 10 minutes to about 15 minutes. A radio frequency of 13.56 MHz in the range from about 20 watts to about 250 watts generates sufficient energy to break the molecular bonds of both the ammonia gas and the siloxane surface.

It will be appreciated by those skilled in the art that in a differently configured plasma chamber, the ammonia flow rate, power, chamber pressure, and exposure time may be outside the ranges of that set forth for the embodiment discussed above. Nevertheless, current experimental testing suggests that the power should relate to the monomer or gas flow rate such that W/FM is in the range from 30–50 megajoules/Kg, where W is the discharge power in joules per second, F is the mass flow rate in moles per second, and M is the molecular weight of a gas (g/mole). However, this value (W/FM) does not take into consideration the power density which is determined by the volume of the plasma chamber. Because the minimum wattage necessary for the plasma polymer of a given monomer differs significantly from that of another monomer at a given pressure, it becomes immediately obvious that W, wattage per square centimeter, or current density alone is not sufficient to describe the conditions of plasma polymerization. Hence, the flow rate, power, and pressure may well be outside of the ranges given.

In light of these stoichimetric relationships, those skilled in the art can readily determine relationships between the flow rate, the pressure, and the exposure times of the siloxane surface to the ammonia.

Ammonia derivatives, existing as free radicals and ions react with each other and with the siloxane surface, thereby introducing amine functionalities onto the siloxane surface. Analysis by electron spectroscopy for chemical analysis ("ESCA") establishes that nitrogen in the form of amine functionalities can be introduced onto the surface on the order of from about three to about seven total atomic percent. ESCA measurements of about three total atomic percent have been found to result in a satisfactory end product. Other polymers not as inert as siloxanes are capable of incorporating much higher amounts of nitrogen.

It should be noted that ESCA analyzes only the top 50–100 angstroms of a surface. Analysis of bulk structure below the sampling depth is not possible with ESCA. In addition, the atomic percent reported by ESCA is for the entire volume analyzed (i.e., the top 50–100 angstroms). Thus, 3% nitrogen detected does not correspond with 3% of the surface atoms being nitrogen. Because of the bulk contribution to the ESCA signal, the actual percent nitrogen atoms on the surface would be significantly greater than 3%.

Nevertheless, ESCA does establish the existence of significant amounts of nitrogen at or near the surface. Moreover, analysis of percent nitrogen provides a valuable approximation for the number of free amines on the surface. The quantity of amines bound to the surface directly affects the coupling efficiency of the PEO or bioactive molecules. Thus, the more amine groups, the more PEO coupling sites.

From the foregoing, it will be appreciated that the parameters associated with ammonia etching are highly interdependent and dependent upon the specific plasma chamber. The following examples illustrate this interdependence. One skilled in the art would appreciate that the parameters described in the following examples can be modified when using a different sized plasma chamber.

EXAMPLE 1

Amine groups were introduced onto the surface of siloxane-coated hollow fibers within the scope of the present invention by plasma etching in the presence of ammonia. A plurality of microporous hollow fibers incorporated into a fully formed intravenous extrapulmonary blood oxygenator were used as the substrate. The fibers were coated with plasma-polymerized siloxane.

The siloxane coated hollow fibers forming the oxygenator were subjected to plasma exposure in the presence of ammonia gas. The entire oxygenator was placed in a plasma chamber. The dimensions of the plasma chamber were fifteen inches long, twelve inches wide and five inches high. The electrodes were in the form of two parallel plates capacitively coupled in the chamber. The oxygenator was subjected to plasma exposure by introducing ammonia gas into the plasma chamber at the flow rate of 190 micromoles per second at 170 mtorr absolute pressure. The hollow fibers were exposed to 180 watts at a radio frequency of 13.56 MHz for fifteen minutes.

According to ESCA analysis, nitrogen in the form of amine functionalities was introduced onto the surface on the order of three total atomic percent. As discussed hereinafter, this amount of nitrogen provides sufficient amine reaction sites for attachment of the PEO and the multifunctional bioactive molecules.

EXAMPLE 2

Amine groups were introduced onto the surface of a siloxane-coated hollow fibers according to the procedure of Example 1, except that fiber sheets, instead of a fully formed oxygenator, are placed in racks between the electrodes. Utilizing the procedures of Example 2, nitrogen in the form of amine functionalities was introduced onto the surface as analyzed by ESCA on the order of six total atomic percent.

Additional examples of introducing amine functionalities by ammonia etching are presented in copending patent application Ser. No. 07/215,014, Examples 1-8 which are incorporated by reference.

2. Introduction of Amine Groups by Plasma Polymerization

Another method for introducing the amine functionalities onto the blood-contacting surface of the siloxane polymer is to introduce the amine groups during the siloxane polymerization itself. This process, known as plasma polymerization or glow discharge polymerization, is achieved by introducing a siloxane monomer vapor and ammonia gas simultaneously in the presence of the plasma. The same type of tubular chamber used for plasma deposition of siloxane may be used for plasma polymerization of siloxane in the presence of ammonia gas.

The process of introducing amine functionalities onto the siloxane surface by plasma polymerization with ammonia gas is discussed in detail in copending patent application Ser. No. 07/215,014, which has been incorporated by reference. For more detailed information about this alternative procedure, specific reference is given to Section C(2) and Examples 9-18 of Ser. No. 07/215,014.

3. Amine Functionalities on the Siloxane Surface

Both ammonia etching and plasma polymerization with ammonia result in amine incorporation into or onto the siloxane polymer. ESCA analysis of the resulting surface demonstrates the existence of Si—H bonds, C-N bonds, amine ($NH_2$) groups, and carbonyl (C=O) groups. In addition, the surface likely includes reactive radicals (e.g., $.CH_2$ and $.NH$). While the exact surface structure resulting from these reaction processes is not known, the resulting surface structure is believed to be a combination of a number of possible bond and group configurations including:

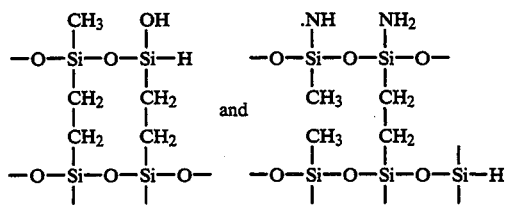

and

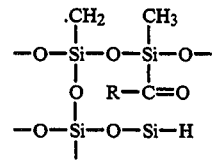

R may be H or OH.

The degree of cross-linking (i.e., the number of bonds formed from methyl radicals on adjacent polymer chains reacting together to form an ethylene unit between chains) is totally dependent upon the reaction parameters. Any polymerization performed using plasma results in a "plasma polymer." The structure of a plasma polymer is significantly different from those resulting from other known polymerization mechanisms; these plasma polymers are by nature "ill-defined."

It will be appreciated that an important aspect of the present invention is the incorporation of amine functionalities (which are available for reaction with PEO) on the blood-contacting surface. Hence, other plasma reaction processes which introduce amine functionalities onto the surface are useful as a part of the present invention.

For example, another possible process for introducing amine functionalities on the blood-contacting surface would be to coat the surface with siloxane monomer in the plasma, and then introduce another polymerizable gas which contains amine groups. One potentially suitable amine-containing polymerizable gas is allylamine.

In addition, depending on the type of siloxane monomer used to form the siloxane surface, nitrogen gas is a suitable alternative to ammonia gas in both the plasma etching and plasma polymerization processes described above. Nitrogen gas initially introduces both amine groups and nitrogen radicals onto the siloxane surface, but upon exposure to water vapor, the nitrogen radicals quickly quench to form amine groups. Because nitrogen is less expensive than ammonia, the use of nitrogen gas can significantly reduce the costs associated with the plasma process described above.

Although the foregoing discussion has focused on the incorporation of amine groups onto the siloxane surface, it will be appreciated that the principles within the scope of the present invention may be readily adapted to incorporate other reactive functional groups onto the siloxane surface.

Thus, an important aspect of the invention is the incorporation of any reactive functional group such as hydroxyl, carbonyl, or carboxylic groups onto the siloxane surface. These functional groups would provide a chemical "handle" on the otherwise inert siloxane surface to which PEO and bioactive molecules may be bound.

The surfaces which emerge from the plasma in any of the processes discussed above are highly reactive. While exact molecular analysis is difficult, the surfaces likely contain some radicals which are available for reacting with almost any species containing double bonds which come into contact with the siloxane surface.

4. Reaction of Amine Functionalities with PEO.

Immediately upon removal from the plasma, the surfaces of the hollow fibers may be reacted with the terminal end groups of unbranched PEO. The PEO functions as an extended flexible spacer to tether bioactive molecules away from, but in close proximity to, the siloxane surface, thereby avoiding problems of steric hindrance of adjacent bioactive molecules which may then be coupled to the siloxane surface. Moreover, as discussed above, the PEO itself also assists in minimizing protein adsorption on the siloxane surface.

A PEO solution is prepared by dissolving poly(ethylene oxide) bis(glycidyl ether) (commonly known as "PEO diglycidyl ether," or "polyoxyethylene diglycidyl ether") in water. The PEO must be in excess to minimize "looping" of the PEO by both reactive ends coupling to the amine groups on the surface. Typical PEO concentrations are in the range from about 5% to about 36%, and preferably about 5% to about 10%.

Poly(ethylene oxide) bis(glycidyl ether) of any molecular weight may be used. However, for maximum protein resistance, the range should be from about 1500 to about 6000 and preferably in the range from about 3000 to about 4000. It has been found that PEO within this molecular weight range minimizes the protein adsorption and maximizes repulsion of platelets and other formed elements from the surface. There is a balance between chain length and stability as well. Longer chains are more susceptible to chain scission. Shorter PEO chains are less flexible, which reduces their protein-resistant properties.

Many terminal reactive groups on PEO may be used depending upon the functionality on the siloxane to which coupling is desired. In addition to epoxide terminated PEO, other suitable terminal groups include 2-(aminoalkyl)-1,4-benzoquinone, bis-(aminediacetic acid), bis-(aminediacetic acid ethyl ester), bis-(aminediacetic acid methyl ester), bis-(aminoacetic acid), bis-(3,5-dioxomorpholine), bis-succinyl-monoamide(monophthalimide), and bis-phosphate(pyrophosphate). In any event, only those PEO chains with two or more reactive functional groups would be available for coupling to a surface and to a bioactive molecule.

In the case of epoxide-terminated PEO, the percent epoxide within the PEO varies depending upon the manufacturer and can vary from about 10% to greater than 75% epoxide. The percentage epoxide directly affects the coupling efficiency. Therefore, if 100% of all PEO chains contain terminal epoxide groups, theoretically all could bind not only to the surface but also be available for binding bioactive molecules.

The plasma-coated fibers of the blood gas exchange device are allowed to sit in the PEO solution, with agitation, for about twelve hours. It has been found that the amount of PEO coupling (as determined by ESCA) does not significantly increase after fifteen hours. In addition, increasing the concentration of PEO (to about 36 weight percent in the solvent) does not significantly increase the amount of coupling over the same time interval. The temperature of the PEO solution is preferably maintained at ambient temperature, in the range from about 20° C. to about 30° C.

After removal from the PEO solution, the coated hollow fibers are rinsed with purified water to remove any unbound PEO. The epoxide groups located at the terminal ends of the PEO chains have reacted with the amine groups located on the siloxane surface as shown below:

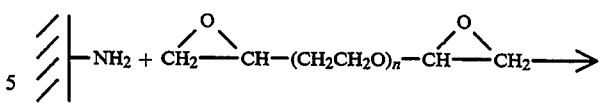

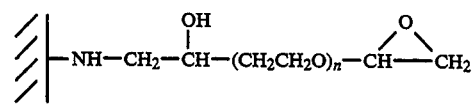

Upon analysis by ESCA, the surface typically contains ether carbon of the carbon 1s spectrum in the range from about 20% to about 50% of the total carbon signal. These carbon atoms on the surface are attributed to PEO attachment to the siloxane surface of the siloxane-coated substrate.

Due to the large excess of PEO used and reaction conditions, only one end of the PEO chain is bound to an amine group on the siloxane surface. As a result, each PEO chain contains an unreacted epoxide group at its unbound end. The epoxide effectively reacts with the electron-rich amine nitrogen because epoxide is a highly strained three-member ring. It also contains an electron depleted carbon atom. The epoxide efficiency is due mainly to the strained ring. In addition, any carbon radicals ($.CH_2$) remaining on the surface following plasma polymerization would not be expected to react with the epoxide groups and would continue to be reactive.

It has been found that the PEO chains may also be suitably terminated with isocyanate functionalities if done under nonaqueous conditions. For a more detailed discussion of the use of isocyanate terminated PEO, reference is made to copending patent application Ser. No. 07/215,014. Other PEO derivatives which should produce suitable results are identified above.

Despite the process used to incorporate the amine functionalities onto the siloxane surface, the PEO can readily react with the amine groups to attach the PEO to the siloxane surface, as shown in Examples 19–71 of copending patent application Ser. No. 07/215,014.

EXAMPLE 3

Siloxane-coated hollow fibers on which amine functionalities have been incorporated onto the siloxane surface according to the procedures of Example 1 were reacted with a solution containing poly(ethylene oxide) bis(glycidyl ether). This PEO solution was prepared by dissolving 18 grams of PEO bis(glycidyl ether) having an average molecular weight of 3,500 in 100 ml of a solvent containing 35 parts formamide and 65 parts purified water.

The hollow fibers were reacted with the PEO solution for ten hours without agitation. The PEO solution temperature was maintained at ambient temperature within the range from about 20° C. to about 30° C. Upon removal from the PEO solution, the hollow fibers were rinsed with 100 ml of purified water to remove any unbound PEO bis(glycidyl ether).

ESCA analysis indicated that 17% of the carbon on the surface of the fiber was in the form of an ether functionality. It was assumed that all ether-type of carbon atoms were due to PEO coupling.

5. PEO Reaction With Bioactive Molecules.

According to the present invention, the unbound end of the PEO is reacted with a quantity of at least one bioactive molecule to covalently bond the bioactive molecules to the PEO which is itself bonded to the gas permeable siloxane surface. An important preferred embodiment of the present invention is to bind the bioactive molecules to the PEO linkages in order to result in a polymer surface having thrombo-resistant properties.

Such bonding of bioactive molecules to the PEO on the siloxane surface of a blood gas exchange device occurs when the device is placed in a solution containing the desired bioactive molecule. One currently preferred bioactive molecule solution is a 5% (wt/vol) heparin/water solution.

The heparin solution is prepared by dissolving heparin in 100 ml phosphate buffered saline (having a pH in the range of from about 7.1 to about 7.5, preferably a pH of about 7.4) resulting in a concentration in the range from about 500 to about 1500 USP units per milliliter. Preferably, the heparin concentration is about 850 USP units per milliliter.

plasmin, and other bioactive pharmaceuticals are coupled to the PEO as shown below.

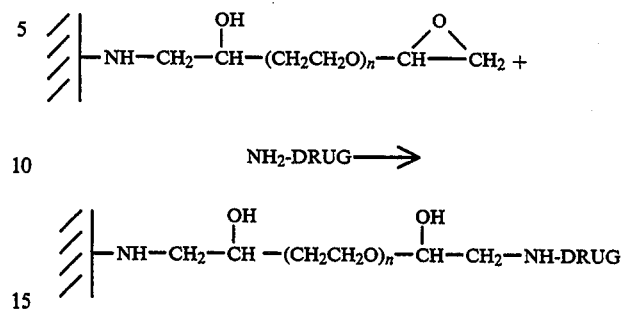

"$NH_2$-DRUG" refers to an amine-containing bioactive molecule. The bioactive molecules are coupled to 2-(aminoalkyl)-1,4-benzoquinone-terminated PEO chains through a similar mechanism shown below.

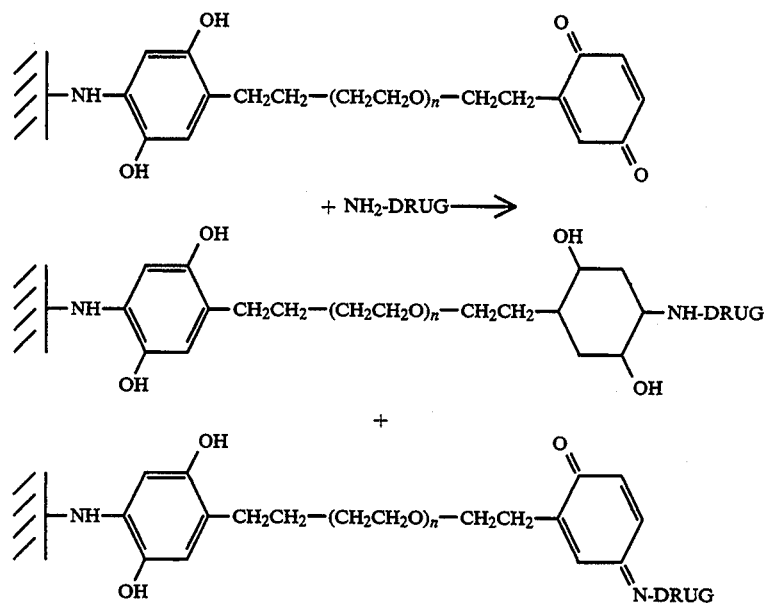

The PEO/siloxane surface is preferably soaked in the heparin solution for about 12 hours with agitation. The heparin solution is maintained at ambient temperature in the range from about 20° C. to about 30° C. Upon removal from the solution, the surface is washed with purified water, air dried, and sterilized with ethylene oxide.

The heparin surface concentration of samples prepared in this manner are found to contain approximately 0.025 $\mu g/cm^2$ of heparin by radio isotope methods. These surfaces are also capable of specifically binding antithrombin III demonstrating their activity. The gas permeability of formed intravenous blood oxygenator devices treated in this way remains significantly greater during operation than untreated microporous hollow fibers or siloxane coated fibers without the PEO and heparin.

It has been found that the heparin, or other bioactive molecules, are coupled to the epoxide groups of the PEO chains through any primary amines available on the bioactive molecule. While the exact mechanism is not known, it is theorized that the heparin, urokinase, Thrombogenicity tests were performed utilizing the "Acute Canine Intra-Arterial Thrombogenicity Assay" procedure described in Mortensen et al., "A Practical Screening Test for Thrombogenicity of Intraarterial Catheters—Preliminary Report," *Artificial Organs*, Vol. 2, Supp., pp. 76–80, 1978, which is incorporated herein by reference. Thrombogenicity testing results have indicated that the heparin molecules are present and active on the surface. Small bundles of treated hollow fibers were implanted into the carotid and femoral arteries of large dogs for a period of 30 minutes. The amount of adherent thrombus and that expelled from the artery following withdrawal of the bundle was weighed and compared with the controls.

Siloxane coated surfaces with PEO and heparin demonstrated an index of 0.016 while control surfaces exhibit an index of 0.060. Statistically significant differences were determined with 95% confidence limits. Other commercially available surfaces with and without heparin were also tested and found to produce indices ranging from 0.002 to 0.250.

The long term efficacy of siloxane coated surfaces with PEO and heparin covalently bound thereto as described above was tested in the Chronic Ovine Intra- Venous Thrombogenicity Assay. Briefly, this assay involves implantation of approximately 20 cm catheter samples into the right and left femoral and jugular veins of 70 kg sheep through multiple venotomies. The catheters are left in place for a period of 15 days with no systemic heparin administered after surgery. The animal is permitted normal activity for a period of 15 days after which heparin is administered prior to sacrificing the animal. The veins are surgically removed and opened to expose the catheter lying in place. The appearance and distribution of the thrombus present is documented photographically. The thrombogenicity score is developed from determination of the thickness of the clot on the catheter, the amount of adherent clot to the vein wall, the amount of free clot in the vein and the percent occlusion of the vein by thrombus. In addition, the catheters are rated by gross thrombus weight for comparison. Each catheter is tested in three animals with a control surface. All data are normalized by analysis of covariance to correct for animal to animal variations. Commercially available catheters with and without other heparin coatings are included in the analyses.

The geometric mean thrombus weights ranged from 544.6 mg to 1754.3 mg for all catheter samples tested. Devices having a siloxane coated surface with PEO and heparin covalently bound thereto within the scope of the present invention produced a means thrombus weight of 544.6 mg, superior to all other catheters tested. This demonstrates that other commercial coatings involving ionically bound heparin were not effective in the inhibition of thrombosis over the 15 day testing period. The observed differences are significant within 90% confidence limits. The amount of thrombus formed on the commercial devices was considerably greater than the amount of thrombus formed on devices having a thrombo-resistant coating within the scope of the present invention.

The data indicate that while some catheters tested were heparin coated, they did not perform significantly better in prevention of thrombus formation than other non-heparinized coatings, and they did not perform as well as devices having a siloxane coated surface with PEO and heparin covalently bound thereto. This follows from a theoretical argument that ionically bound heparin will leach from a surface and become depleted within a very short time. The thrombo-resistant coating within the scope of the present invention, which covalently binds heparin to the siloxane surface through a PEO linkage, was the only heparinized coating catheter to maintain heparin activity over the 15 day testing period.

Not only should the thrombo-resistant coatings within the scope of the present invention inhibit thrombus formation, but also maintain suitable gas permeability over time. Intravenous blood oxygenator devices containing microporous hollow fibers coated with a siloxane membrane and treated with PEO and heparin within the scope of the present invention were implanted in the vena cavae of sheep. The oxygenator devices maintained suitable gas transfer over a period of nineteen days with less than 10% loss of efficiency.

E. Summary

In summary, the thrombo-resistant compositions and methods disclosed herein are capable of counteracting blood-material incompatibility reactions without inhibiting the gas permeability of the blood-contacting surface. This is accomplished by immobilizing a quantity of at least one bioactive molecule which counteracts a specific blood material incompatibility reaction to the blood-contacting siloxane surface through individual poly(ethylene oxide) spacer chains. Because the bioactive molecules are tethered away from the blood-contacting surface, the molecules avoid problems of steric hindrance and possess an activity approaching the activity in solution. In addition, the bioactive molecules are covalently bound to the blood-contacting surface, thereby eliminating leaching of the bioactive molecules into the blood plasma and prolonging the effectiveness of the thrombo-resistant composition.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for producing a thrombo-resistant coating for use on gas permeable surfaces which contact blood, the method comprising the steps of:
   (a) obtaining a gas permeable material having a gas permeable siloxane surface onto which a plurality of amine functional groups have been bonded;
   (b) reacting the amine functional groups on the siloxane surface with poly(ethylene oxide) chains terminated with functional groups capable of reacting with the amine functional groups on the siloxane surface, thereby resulting in a product having single poly(ethylene oxide) chains which are bonded to corresponding single amine functional groups, said product being gas permeable;
   (c) reacting the product of step (b) with at least one bioactive molecule capable of counteracting at least one blood-material incompatibility reaction such that a single bioactive molecule is correspondingly coupled to a single poly(ethylene oxide) chain, thereby resulting in a gas permeable siloxane surface to which are attached, by a poly(ethylene oxide) chain, a plurality of the at least one bioactive molecule which react with blood components which come in proximity to the siloxane surface of the gas permeable material in order to resist at least one blood-material incompatibility reaction.

2. A method for producing a thrombo-resistant coating for use on gas permeable surfaces which contact blood as defined in claim 1, wherein the step of obtaining a gas permeable material having a siloxane surface onto which a plurality of amine functional groups have been bonded comprises the steps of:
   introducing ammonia gas within a plasma chamber capable of performing plasma etching;
   exposing the ammonia gas to a radio frequency of sufficient power to create a plasma; and
   exposing the siloxane surface to the ammonia plasma for sufficient time to introduce amine functional groups onto the siloxane surface.

3. A method for producing a thrombo-resistant coating for use on gas permeable surfaces which contact blood as defined in claim 2, further comprising the step of obtaining a microporous hollow fiber having a siloxane surface thereon.

4. A method for producing a thrombo-resistant coating for use on gas permeable surfaces which contact blood as defined in claim 1, wherein the poly(ethylene oxide) chains terminated with functional groups capable of reacting with the amine functional groups comprises poly(ethylene oxide) bis(glycidyl ether).

5. A method for producing a thrombo-resistant coating for use on gas permeable surfaces which contact blood as defined in Claim 1, wherein the poly(ethylene oxide) chains terminated with functional groups capable of reacting with the amine functional groups comprises poly(ethylene oxide) 2-(aminoalkyl)-1,4-benzoquinone.

6. A method for producing a thrombo-resistant coating for use on gas permeable surfaces which contact blood as defined in claim 1, wherein the product of step (b) is reacted with a solution of at least one bioactive molecule capable of resisting at least one of the following blood-material incompatibility reactions: extrinsic coagulation pathway activation, platelet destruction and injury, platelet adhesion activation, platelet aggregation, thrombus formation, complement activation, contact system activation, and fibrinolytic system activation.

7. A method for producing a thrombo-resistant coating for use on gas permeable surfaces which contact blood as defined in claim 1, wherein the product of step (b) is reacted with heparin.

8. A method for producing a thrombo-resistant coating for use on gas permeable surfaces which contact blood as defined in claim 1, wherein the product of step (b) is reacted with at least one bioactive molecule selected from the group consisting of heparin, urokinase, plasmin, and ticlopidine.

9. A method for producing a thrombo-resistant coating for use on gas permeable surfaces which contact blood as defined in claim 1, wherein the product of step (b) is reacted with at least one bioactive molecule selected from the group consisting of heparin, urokinase, and prostaglandin $E_1$.

10. A method for producing a thrombo-resistant coating for use on gas permeable surfaces which contact blood as defined in claim 1, wherein the product of step (b) is reacted with at least one bioactive molecule selected from the group consisting of heparin, plasmin, and ticlopidine.

11. A method for producing a thrombo-resistant coating for use on gas permeable surfaces which contact blood as defined in claim 1, wherein the product of step (b) is reacted with at least one bioactive molecule selected from the group consisting of heparin, urokinase, plasmin, prostaglandin $E_1$, and ticlopidine.

12. A method for producing a thrombo-resistant coating for use on gas permeable surfaces which contact blood, the method comprising the steps of:
(a) obtaining a gas permeable material having a siloxane surface;
(b) introducing ammonia gas within a plasma chamber capable of performing plasma etching;
(c) exposing the ammonia gas to a radio frequency of sufficient power to create a plasma;
(d) exposing the siloxane surface to the ammonia plasma for sufficient time to introduce amine functional groups onto the siloxane surface, thereby resulting in a product having a plurality of amine functional groups bonded onto the siloxane surface;
(e) reacting the product of step (d) with a solution having a plurality of poly(ethylene oxide) spacer chains, having the following general formula $$R_1-(CH_2CH_2O)_n-R_2$$

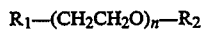

wherein $R_1$ and $R_2$ are suitable functional groups capable of reacting with the amine functional groups on the siloxane surface; and
(f) reacting the product of step (e) with a solution of at least one bioactive molecule capable of counteracting specific blood-material incompatibility reactions such that a single bioactive molecule is correspondingly coupled to a single poly(ethylene oxide) spacer chain, thereby resulting in a siloxane surface to which are attached, by a poly(ethylene oxide) chain, a plurality of the at least one bioactive molecules which react with blood components which come in proximity to the surface of the material in order to resist at least one blood-material incompatibility reaction.

13. A method for producing a thrombo-resistant coating for use on gas permeable surfaces which contact blood as defined in claim 12, wherein $R_1$ and $R_2$ comprises glycidyl ether.

14. A method for producing a thrombo-resistant coating for use on gas permeable surfaces which contact blood as defined in claim 12, wherein $R_1$ and $R_2$ comprise 2-(aminoalkyl)-1,4-benzoquinone.

15. A method for producing a thrombo-resistant coating for use on gas permeable surfaces which contact blood as defined in claim 12, wherein the product of step (e) is reacted with heparin.

16. A method for producing a thrombo-resistant coating for use on gas permeable surfaces which contact blood as defined in claim 12, wherein the product of step (e) is reacted with a plurality of at least one bioactive molecule selected from the group consisting of heparin, urokinase, plasmin, and ticlopidine.

17. A method for producing a thrombo-resistant coating for use on gas permeable surfaces which contact blood as defined in claim 12, wherein the product of step (e) is reacted with a plurality of at least one bioactive molecule selected from the group consisting of heparin, urokinase, plasmin, ticlopidine, and prostaglandin $E_1$.

18. A thrombo-resistant composition for use on gas permeable surfaces which contact blood comprising:
a gas permeable material having a siloxane surface onto which a plurality of at least one bioactive molecule are covalently bonded, said at least one bioactive molecule counteracting at least one specific blood-material incompatibility reaction when the blood comes into proximity of the surface of the material; and
a plurality of poly(ethylene oxide) chains covalently bonded to the bioactive molecules and covalently bonded to the siloxane surface such that a single bioactive molecule is correspondingly coupled to a single poly(ethylene oxide) chain which in turn is bonded to the gas permeable siloxane surface.

19. A thrombo-resistant composition for use on gas permeable surfaces which contact blood as defined in claim 18, wherein the at least one bioactive molecule is capable of resisting at least one of the following blood material incompatibility reactions: extrinsic coagulation pathway activation, platelet destruction and injury, platelet adhesion, platelet aggregation, thrombus formation, and complement activation.

20. A thrombo-resistant composition for use on gas permeable surfaces which contact blood as defined in claim 18, wherein the at least one bioactive molecule is heparin.

21. A thrombo-resistant composition for use on gas permeable surfaces which contact blood as defined in claim 18, wherein the at least one bioactive molecule is selected from the group consisting of heparin, urokinase, plasmin, ticlopidine, and prostaglandin $E_1$.

22. A thrombo-resistant composition for use on gas permeable surfaces which contact blood, the composition being made by a process comprising the steps of:
(a) obtaining a gas permeable material having a siloxane surface onto which a plurality of amine functional groups have been bonded;
(b) reacting the amine functional groups on the siloxane surface with poly(ethylene oxide) chains terminated with functional groups capable of reacting with the amine functional groups on the siloxane surface such that a single poly(ethylene oxide) chain is bonded to a corresponding single amine functional group; and
(c) reacting the product of step (b) with heparin such that a single heparin molecule is covalently bonded to a single poly(ethylene oxide) chain, thereby resulting in a siloxane surface to which are attached, by a poly(ethylene oxide) chain, a plurality of heparin molecules capable of reacting with blood components which come in proximity to the siloxane surface of the material in order to resist at least one blood-material incompatibility reactions.

23. A thrombo-resistant composition for use on gas permeable surfaces which contact blood as defined in claim 22, wherein the poly(ethylene oxide) chains terminated with functional groups capable of reacting with the amine functional groups comprises poly(ethylene oxide) bis(glycidyl ether).

24. A thrombo-resistant composition for use on gas permeable surfaces which contact blood as defined in claim 22, wherein the poly(ethylene oxide) chains terminated with functional groups capable of reacting with the amine functional groups comprises poly(ethylene oxide) 2-(aminoalkyl)-1,4-benzoquinone.

25. A thrombo-resistant composition comprising a plurality of compounds having the formula

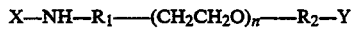
X—NH—R$_1$——(CH$_2$CH$_2$O)$_n$——R$_2$—Y wherein X is a siloxane surface; and wherein R$_1$ are R$_2$ are the residue resulting from a reaction between a poly(ethylene oxide) terminal group capable of reacting with an amine and capable of reacting with a bioactive molecule, respectively; and wherein Y is a bioactive molecule capable of counteracting a specific blood material incompatibility reaction.

26. A thrombo-resistant composition as defined in claim 25, wherein R$_1$ is

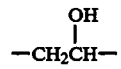
$$-CH_2\overset{OH}{\underset{|}{C}}H-$$

and wherein R$_2$ is

$$-\overset{OH}{\underset{|}{C}}HCH_2-.$$

27. A thrombo-resistant composition as defined in claim 25, wherein Y is heparin.

28. A thrombo-resistant composition as defined in claim 25, wherein Y is heparin, ticlopidine, or urokinase.

29. A thrombo-resistant composition as defined in claim 25, wherein Y is heparin, prostaglandin $E_1$, plasmin, urokinase, or tissue plasminogen activator.

30. A thrombo-resistant composition as defined in claim 25, wherein Y is heparin, ticlopidine, plasmin, urokinase, tissue plasminogen activator, or FUT-175.

31. A thrombo-resistant composition as defined in claim 25, wherein Y is capable of resisting either extrinsic coagulation pathway activation, platelet destruction and injury, platelet adhesion, platelet aggregation, thrombus formation, or complement activation.

32. An apparatus for effecting extrapulmonary blood gas exchange comprising:
a plurality of gas permeable tubes, each tube having a proximal end and a distal end, said gas permeable tubes being coated with a thrombo-resistant composition comprising a plurality of compounds having the formula

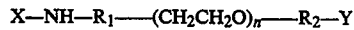
X—NH—R$_1$——(CH$_2$CH$_2$O)$_n$——R$_2$—Y wherein X is a siloxane surface on a gas permeable tube; and wherein R$_1$ are R$_2$ are the residue resulting from a reaction between a poly(ethylene oxide) terminal group capable of reacting with an amine and capable of reacting with a bioactive molecule, respectively; and wherein Y is a bioactive molecule capable of counteracting at least one blood-material incompatibility reaction;
a dual lumen coaxial tube comprising an inner lumen and an outer lumen, said inner lumen extending between the proximal and distal ends of the gas permeable tubes and said outer lumen terminating adjacent to the proximal ends of the gas permeable tubes and the inner lumen terminating adjacent to the distal ends of the gas permeable tubes, such that the gas permeable tubes are in gaseous communication with both the inner lumen and the outer lumen;
means for introducing oxygen from the inner lumen into the distal ends of the gas permeable tubes whereby blood in contact with the gas permeable tubes receives oxygen from the gas permeable tubes and releases carbon dioxide gas to the gas permeable tubes; and
means for collecting carbon dioxide at the proximal ends of the gas permeable tubes and introducing said carbon dioxide into the outer lumen for removal therethrough.

33. An apparatus for effecting extrapulmonary blood gas exchange as defined in claim 32, wherein the at least one bioactive molecule comprises heparin.

* * * * *

UNITED STATES PATENT AND TRADEMARK OFFICE
CERTIFICATE OF CORRECTION

PATENT NO.   : 5,338,770
DATED        : August 16, 1994
INVENTOR(S)  : SUZANNE WINTERS et al.

It is certified that error appears in the above-identified patent and that said Letters Patent is hereby corrected as shown below:

```
Column 4, line 25, "breakdown" should be --break down--
Column 4, line 51, "practive" should be --practice--
Column 7, lines 63-64, "preproducing" should be --reproducibly--
Column 8, line 6, "for" should be --For--
Column 11, line 14, delete "a"
Column 17, line 27, "means" should be --mean--
Column 21, line 27, "reactions" should be --reaction--
Column 21, line 47, "are" should be --and--
```

Signed and Sealed this

Eleventh Day of April, 1995

Attest:

BRUCE LEHMAN

*Attesting Officer*   *Commissioner of Patents and Trademarks*